(12) United States Patent
Mungi et al.

(10) Patent No.: US 10,058,575 B2
(45) Date of Patent: Aug. 28, 2018

(54) PROBIOTIC COMPOSITION COMPRISING THE NOVEL ISOLATED BACTERIAL STRAIN OF BREVIBACTERIUM CASEI AP9

(71) Applicant: COUNCIL OF SCIENTIFIC & INDUSTRIAL RESEARCH, New Delhi (IN)

(72) Inventors: Hrishikesh Vinayak Mungi, Maharashtra (IN); Pooja Vijay Ghushe, Maharashtra (IN); Avinash Vellore Sunder, Maharashtra (IN); Archana Vishnu Pundle, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 158 days.

(21) Appl. No.: 14/913,497

(22) PCT Filed: Aug. 22, 2014

(86) PCT No.: PCT/IN2014/000541
§ 371 (c)(1),
(2) Date: Feb. 22, 2016

(87) PCT Pub. No.: WO2015/025336
PCT Pub. Date: Feb. 26, 2015

(65) Prior Publication Data
US 2016/0213718 A1  Jul. 28, 2016

(30) Foreign Application Priority Data

Aug. 22, 2013  (IN) .......................... 2473/DEL/2013

(51) Int. Cl.
| | | |
|---|---|---|
| A61K 35/74 | (2015.01) | |
| A61K 38/46 | (2006.01) | |
| A61K 35/741 | (2015.01) | |
| C12R 1/13 | (2006.01) | |
| A23L 33/00 | (2016.01) | |
| A23L 33/135 | (2016.01) | |

(52) U.S. Cl.
CPC .......... *A61K 35/741* (2013.01); *A23L 33/135* (2016.08); *A23L 33/30* (2016.08); *C12R 1/13* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,080,401 A | * | 6/2000 | Reddy .................. | A61K 36/235 424/725 |
| 9,028,841 B2 | * | 5/2015 | Henn ..................... | A61K 38/13 424/203.1 |
| 9,603,878 B2 | * | 3/2017 | Berry ................... | A61K 9/0031 |
| 2016/0213718 A1 | * | 7/2016 | Mungi ................... | C12R 1/13 |
| 2017/0151291 A1 | * | 6/2017 | Henn ..................... | A61K 35/742 |
| 2018/0015130 A1 | * | 1/2018 | Berry ................... | A61K 35/741 |
| 2018/0071344 A1 | * | 3/2018 | Berry ................... | A61K 9/0031 |

FOREIGN PATENT DOCUMENTS

| | | |
|---|---|---|
| EP | 0 416 892 A1 | 3/1991 |
| WO | WO 2010/014541 A2 | 2/2010 |
| WO | WO-2015077794 A1 * 5/2015 | .............. C12N 1/20 |

OTHER PUBLICATIONS

Kiran et al, FEMS Immunology and Medical Microbiology, Aug. 2010, 59/3:432-438 (Year: 2010).*
Cai et al, International Journal of Systematic Bacteriology, Jul. 1994, 44/3:583-585 (Year: 1994).*
Iannitti et al, Clinical Nutrition, 2010, 29:701-725 (Year: 2010).*
Bittner et al, Clinical Therapeutics, 2007, 29/6:1153-1160; online publication Jun. 22, 2007 (Year: 2007).*
International Search Report (ISR) for PCT/IN2014/000541; I.A. fd: Aug. 22, 2014, dated May 7, 2015, European Patent Office, Rijswijk, Netherlands.
International Preliminary Report on Patentability (IPRP) including the Written Opinion of the International Searching Authority (PCT Rule 44bis) for PCT/IN2014/000541; I.A. fd: Aug. 22, 2014, dated Feb. 23, 2016, by the International Bureau of WIPO, Geneva, Switzerland.
Kiran, GS et al.," Biofilm disruption potential of a glycolipid biosurfactant from marine *Brevibacterium casei*," FEMS Immunol Med Microbiol. Aug. 2010;59(3):432-438. doi: 10.1111/j.1574-695X.2010.00698.x. Epub May 12, 2010, Blackwell Publishing Ltd.
Garcia, JL et al, "Catabolism and biotechnological applications of cholesterol degrading bacteria," Microbial Biotechnology. Nov. 2012;5(6):679-699. doi:10.1111/j.1751-7915.2012.00331.x. Epub Feb. 7, 2012, Blackwell Publishing Ltd.
Bezkorovainy, A, "Probiotics: determinants of survival and growth in the gut" Am J Clin Nutr. Feb. 2001;73(2 Suppl):399S-405S, American Society of Clinical Nutrition, Bethesda, MD.
Ooi, L-G et al., "Cholesterol-lowering effects of probiotics and prebiotics: a review of in vivo and in vitro findings," Int J Mol Sci, Jun. 17, 2010;11(6):2499-522, doi: 10.3390/ijms11062499, MDPI, Basel, Switzerland.

* cited by examiner

*Primary Examiner* — Nita M Minnifield
(74) *Attorney, Agent, or Firm* — Sterne, Kessler, Goldstein & Fox P.L.L.C.

(57) ABSTRACT

The present invention discloses a novel isolated bacterial strain exhibiting probiotic properties. More particularly, the invention discloses a probiotic composition comprising *Brevibacterium casei* AP9 MCC0012 having improved pH and bile tolerance and improved antimicrobial properties as well as possessing cholesterol reduction property.

10 Claims, 2 Drawing Sheets

US 10,058,575 B2

Figure 1:
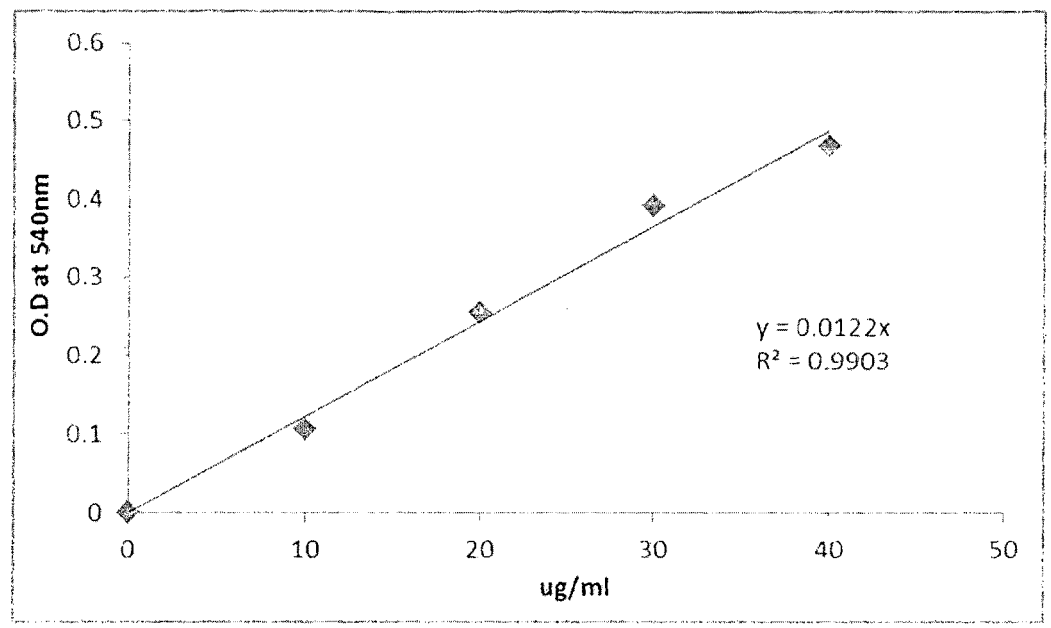

PROBIOTIC COMPOSITION COMPRISING THE NOVEL ISOLATED BACTERIAL STRAIN OF BREVIBACTERIUM CASEI AP9

FIELD OF THE-INVENTION

The present invention relates to a novel isolated bacterial strain of *Brevibacterium casei* AP9 MCC0012 exhibiting bile salt hydrolase (BSH) activity, improved pH and bile tolerance as well as possessing anti-microbial properties. In particular, the present invention relates to a composition comprising *Brevibacterium casei* MCC0012, either alone or in combination with one or more probiotic organisms, or an agent that may enhance the probiotic activity of *Brevibacterium casei* MCC0012. Further, the present invention provides administration of *Brevibacterium casei* AP9 MCC0012 in the probiotic composition to a subject in need for lowering cholesterol levels.

BACKGROUND OF THE INVENTION AND DESCRIPTION OF PRIOR ART

The term "probiotics" was first introduced in 1953 by Werner Kollath. It is defined as "A live microbial feed supplement which beneficially affects the host animal by improving its intestinal microbial balance". Subsequently, many probiotic products have been introduced in the market. The global probiotic products market was estimated at $24.23 billion in 2011. More than 500 probiotic F&B products have been introduced in the past decade.

Currently, *Lactobacillus* strains dominate the probiotics' market. Further, the marketed products containing *Lactobacillus* usually comprise a combination of 3-5 organisms. This combination is required since no single organism possesses desirable characteristics for probiotics namely, acidic stability, intestinal stability, stability in presence of bile, pancreatin and such like, good adhesion property and cholesterol reducing or lipid degradation property due to production of Bile salt hydrolase (BSH). *Lactobacillus* suffers from several drawbacks such as poor pH tolerance, poor bile tolerance and indifferent survival in gastric and intestinal juices. Therefore, there is a continuous quest for organisms with improved properties such as improved pH tolerance and better survival in gastric and intestinal juices. Further, the organisms with improved anti microbial properties will be an added benefit while proposing probiotic compositions.

Some more desirable characteristic of probiotic organisms include survival in presence of preservatives and BSH or Bile salt hydrolase, which is known to reduce serum cholesterol. This does not allow reabsorption of cholesterol and reduction of cholesterol by enterohepathic pathway. Therefore, increased BSH production is a desirable characteristic from a probiotic organism.

The *Brevibacterium casei* AP9 strain has been explored for the Biosyntheis of Cobalt oxide nano particles, as reported in an article titled "Extracellular Bacterial Synthesis of Protein-Functionalized Ferromagnetic $Co_3O_4$ Nanocrystals and Imaging of Self-Organization of Bacterial Cells under Stress after Exposure to Metal Ions" by Umesh Kumar, Ashvini Shete, Arti S. Harle, Oksana Kasyutich, W. Schwarzacher, Archana Pundle and Pankaj Poddar in Nanobiotechnology *Chem. Mater.* 2008, 20, 1484-1491. But this organism has not been explored for its probiotic properties.

Thus, as per the above mentioned drawbacks of the hitherto reported prior arts, the inventors of the present invention realized that there is an unmet need in the art for probiotic microorganisms with better properties such as improved pH tolerance, enhanced survival in gastric and intestinal juices, while exhibiting improved anti-microbial properties and better BSH production activity.

OBJECTS OF THE INVENTION

The main objective of the present invention is thus to provide a probiotic composition comprising probiotic microorganisms that obviates the drawbacks of the hitherto reported prior art.

Another object of the present invention is to provide a probiotic composition wherein the organism is resistant to bile, acid, gastric and intestinal juices while possessing antimicrobial properties.

Still another object of the present invention is to provide a novel isolated bacterial strain of *Brevibacterium casei* AP9 MCC0012 having the aforesaid properties.

Yet another object of the present invention is to provide a process for screening multiple strains of bacteria collected from marine water and sediment samples so as to isolate *Brevibacterium casei* AP9 having better survival rate in gastric and intestinal juices and exhibiting better BSH production activity.

SUMMARY OF THE INVENTION

The present invention relates to a probiotic composition comprising *Brevibacterium casei* AP9 MCC0012 useful as a probiotic for the alleviation or treatment of gastric disorders. The instant probiotic compositions comprising *Brevibacterium casei* exhibit acid-tolerant property, i.e. the stability of *B. casei* in the presence of gastric acids and intestinal fluids, adhesion of *B. casei* in presence of gastric fluids, bile salt tolerance as well as possess Bile Salt Hydrolase (BSH) activity. Thus, the said probiotic composition comprising *B. casei* may be used in cholesterol reduction and anti-microbial therapy.

In line with the above, the present invention provides novel probiotic compositions comprising *Brevibacterium casei* AP9 which has improved bile, gastric and intestinal juice tolerance.

In another aspect, the invention provides novel probiotic compositions comprising *Brevibacterium casei* AP9 optionally along with other probiotic organisms to provide improved probiotic activity.

In yet another aspect, the invention provides novel probiotic compositions with improved bile, gastric and intestinal juice tolerance and better BSH production activity.

In still another aspect, the invention provides novel probiotic compositions with improved anti microbial properties.

The novel probiotic organism according to the invention is *Brevibacterium casei* AP9 MCC0012.

The novel probiotic composition comprising *Brevibacterium casei* AP9 MCC0012 according to the invention has improved bile tolerance.

The novel probiotic composition comprising *Brevibacterium casei* AP9 MCC0012 according to the invention provides improved gastric and intestinal juice tolerance.

In an additional aspect, the probiotic composition of the instant invention reduces serum cholesterol levels in a subject, wherein in a preferred aspect, the subject is mammal.

In yet another aspect, the present invention provides a novel probiotic composition comprising *Brevibacterium casei* AP9 MCC0012 useful in the manufacture of a medicament for providing probiotic therapy meant for treating/controlling bacterial diseases or digestive diseases or to reduce cholesterol levels in a subject which method comprises administering *Brevibacterium casei* AP9 MCC0012 in a therapeutically effective amount to a subject in need thereof.

In a further aspect, the invention provides a method of providing probiotic therapy for treating/controlling bacterial diseases or digestive diseases which method comprises administering *Brevibacterium casei* AP9 MCC0012 in a therapeutically effective amount to a subject in need thereof.

In another aspect, the invention provides a method for reducing cholesterol levels in a subject comprises administering *Brevibacterium casei* AP9 MCC0012 to a subject in need thereof in an effective amount to reduce the cholesterol levels.

In yet another aspect, *Brevibacterium casei* AP9 MCC0012 may be administered in doses ranging from 0.01-99.9% of the composition to a subject in need for lowering cholesterol levels.

BRIEF DESCRIPTION OF THE ACCOMPANYING DRAWINGS

Figure 2:
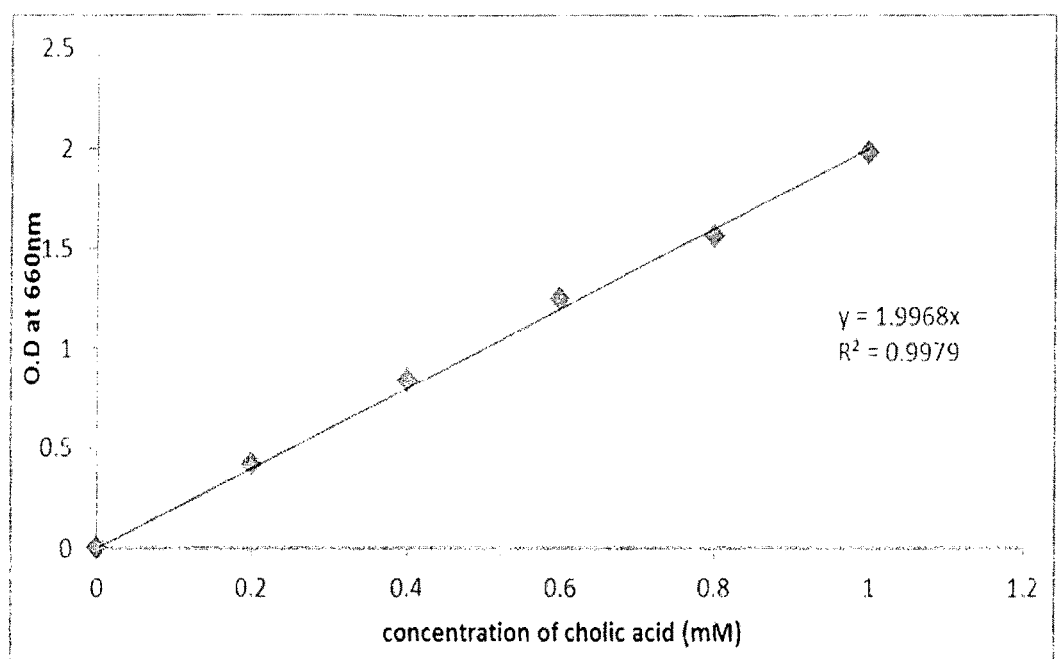

FIG. 1 depicts standard graph for cholesterol detection.
FIG. 2 depicts standard graph for cholic acid detection.

DETAILED DESCRIPTION OF THE INVENTION

The invention will now be described in detail in connection with certain preferred and optional embodiments, so that various aspects thereof may be more fully understood and appreciated.

The novel probiotic organism according to the invention is *Brevibacterium casei* AP9, deposited under Budapest treaty in International Depository, Microbial Culture Center, Pune, Maharastra, India, on 10 May 2013, which has been accorded the Accession number MCC0012.

*Brevibacterium casei* is a Gram positive rod shaped bacterium (2-3 μM×0.2-0.3 μM). It produces enzymes like BSH, amylase, N-acylhomoserine lactone acylase. It can produce $Co^{2+}$ nanoparticles extracellularly, it can tolerate 15-18% NaCl.
Depository Information from MCC(NCCS)
Deposited culture: *Brevibacterium Casei* AP-9
Accession Number: MCC0012

The present invention provides novel isolated bacterial strain of *Brevibacterium casei* AP9 from marine sources and sediment samples collected from western coastal areas of India located at coastal areas of Arabian sea near Alibag (18.6414°N, 72.8722°E) Pincode of Alibag: 402201 while screening many strains for a probiotic with desired qualities.

The preparation of the probiotic formulation was carried out in the following manner:
 a. Drying of the cell pellet to powder form—24 hrs old culture of *Brevibacterium casei* AP9 MCC0012 having 1×10⁶ CFU/ml was centrifuged at 8000 rpm for 10 min. The pellet was re-suspended in skimmed milk and the suspension centrifuged at 8000 rpm for 10 min. The resultant pellet was dispersed in different ampules and lyophilised.
 b. Selection of Hydrocolloid—An appropriate hydrocolloid was selected based on toxicity and added to the cell pellet obtained in step [a] so as to provide stability to the prepared formulation.
 c. Process of encapsulation was carried out by extrusion or emulsion method.

In an embodiment, *Brevibacterium casei* AP9 was evaluated for bile salt hydrolase production using ninhydrin assay. Accordingly, *Brevibacterium casei* AP9 along with some unidentified marine isolates and some commercially available microorganisms that are penicillin resistant and belong to *Lactobacillus* species were tested for bile salt hydrolase production. It was observed that amongst the 5 isolated marine bacterial strains; 7 commercially available strains of *Lactobacillus* (*L. plantarum* ATCC.NO-8014, *L. fermentum* ATCC.NO-9338, *L. acidophillus* ATCC.NO-11975, *L. casei* ATCC.NO-335, *L. bulgarius* ATCC.NO-8001, *L. lactis* ATCC.NO-10705, *L. lechimanni* ATCC.NO-4797) and 1 commercially available penicillin acylase producing strain (*Bacillus cereus* ATCC. No JN183063), the *Brevibacterium casei* AP9 (Accession No: MCC0012) showed highest BSH activity of 2-2.5 IU.

In another embodiment, *Brevibacterium casei* AP9 showed survival and BSH activity of 1-1.5 IU, when tested for acid tolerance. The bile salt tolerance test yielded that *Lactobacillus* strains (example 3b) showed tolerance of 2% with activity of 0.1-0.5 IU, penicillin acylase producing strain (example 3b) showed 5% tolerance with activity of 0.1-2 IU, 2 marine strains showed 3% and 7% tolerance with activity of 0.1-2.5 IU and 0.1-2 IU respectively and *Brevibacterium Casei* AP9 (Accession No: MCC0012) showed a tolerance of 1% with activity of 0.75-1.25 IU. These results were considered in favour of *Brevibacterium Casei* AP (Accession No: MCC0012) as human gut has 0.3% concentration of bile salts. Though other strains produce higher BSH activity in presence of higher bile salts, actually the level of bile salts is restricted to 0.3-0.5% in human gut. Hence it is desirable that a probiotic organism produces high BSH activity at the said concentration. Hence higher production of BSH at high concentration is not desirable compromising other probiotic properties. So with respect to bile salt tolerance at 1% concentration AP9 produces better activity of 0.75-1.25 IU.

In yet another embodiment, the sodium chloride tolerance of *Brevibacterium casei* AP9 (Accession No: MCC0012) was tested and it was found that *Brevibacterium casei* AP9 has maximum tolerance of 18-22% with BSH activity of 1.75-2.5 IU. *Lactobacillus* strain (refer example 3b) showed a tolerance of 6-8% with activity of 1.5-2 IU and penicillin acylase producing strain (refer example 3b) exhibited 8-10% tolerance with activity of 1.75-2.5 IU sodium chloride tolerance when compared with *B. casei* AP9.

In still another embodiment, the formulation comprises $10^5$ to $10^9$ CFU/ml of *Brevibacterium casei* AP9 MCC0012.

In a further embodiment, the isolated bacterial strains are resistant to gastric and intestinal fluids. In a preferred embodiment, the organisms are found to be resistant to gastric and intestinal fluids when tested after washing with saline or skimmed milk.

In yet another aspect, the organism, *Brevibacterium casei* AP9 MCC0012 possesses improved adhesion property.

In one more aspect, the organism, *Brevibacterium casei* AP9 MCC0012 possesses anti microbial activity.

In an embodiment, the invention discloses a probiotic composition comprising *Brevibacterium casei* AP9 MCC0012, either alone or in combination with other organisms, or an agent that may enhance the probiotic activity of *Brevibacterium casei* AP9. The composition may be presented in solid, liquid or semi solid form and may be taken by routes selected from oral, parenteral, intra vaginal or rectal The probiotic composition according to the invention additionally comprises one or more suitable pharmaceutical/neutraceutical excipients/carriers to provide the same in a desired dosage form to achieve desired delivery. The suitable pharmaceutical/neutraceutical excipients may be selected from the group consisting of diluents, binders, polymers, fillers, vehicles, carriers, disintegrants.

In a preferred embodiment, a composition comprising Brevibacterium casei AP9 optionally in combination with one or more probiotics selected from the group consisting of L. plantarum ATCC.NO-8014, L. fermentum ATCC.NO-9338, L. acidophillus ATCC.NO-11975, L. casei ATCC.NO-335, L. bulgarius ATCC.NO-8001, L. lactis ATCC.NO-10705, L. lechimanni ATCC.NO-4797 and Bacillus cereus ATCC. No JN183063 is disclosed. The composition possesses enhanced probiotic properties and has improved gastric and intestinal juice tolerance.

In another embodiment, Brevibacterium casei AP9 may be administered in doses ranging from 0.01-99.9% of the composition to a subject in need of a probiotic therapy.

In still another embodiment of the invention, the hydrocolloids may be selected from the group consisting of alginate, whey protein, gelatin, carrageenan and the like.

In yet another embodiment, the invention provides a method of providing probiotic therapy for treating/controlling bacterial diseases or digestive diseases which method comprises administering Brevibacterium casei MCC0012 in a therapeutically effective amount to a subject in need thereof.

The digestive diseases on which the efficacy of the developed probiotic composition were evaluated are selected from the group consisting of irritable bowel syndrome, diarrhea, vaginal and urinary infections, ulcerative colitis, Crohn's disease and the recurrence of pouchitis.

In yet another embodiment, Brevibacterium casei AP9 MCC0012 may be administered in doses ranging from 0.01-99.9% of the composition to a subject in need for lowering cholesterol levels.

In still another embodiment, the invention provides a method for reducing cholesterol levels in a subject which method comprises administering Brevibacterium casei MCC0012 in a therapeutically effective amount to a subject in need thereof. The therapeutically effective amount is the amount required to achieve desired therapeutic effect in a subject while undergoing probiotic therapy.

In a further embodiment, the compositions of the invention are stable over wide range of gastric to intestinal pH, non toxic and possess shelf life as desired.

EXAMPLES

The following examples are given by way of illustration and therefore should not be construed to limit the scope of the present invention.

Example 1: Isolation of Organisms

Marine water and sediment samples were collected from the coastal areas of Arabian sea near Alibag (18.6414°N, 72.8722°E) PIN 402201, India. Surface water samples (Approx 1 L) and sediment samples were collected from five different locations (total 10 samples), 0.2 km away from the beach. Collected samples were stored at 4° C. until further use. Media used for isolation of marine strain was Zobell Marine Media (Himedia). All 5 surface water samples were pooled and mixed thoroughly. From pooled samples 3 aliquots were used for processing. Aliquots were serially diluted to $10^{-2}$, $10^{-4}$, $10^{-6}$ and $10^{-8}$ and 100 µl from each serial dilution was spread on Zobell Marine agar medium plates. Plates were incubated at 28° C. for 7 days. After every 24 hrs interval, colony morphotype on each plate was observed. 15 strains from marine water and sediment samples were isolated, out of which AP9 (Brevibacterium casei) was found to be a potential Bile Salt Hydrolase (BSH) producer.

Example 2: BSH Production and Determination

Production of BSH

Production was carried out by growing AP9 in various medium like Zobell marine medium (Himedia) and varying concentration of Nutrient Broth (NB) medium (1% w/v peptone (Himedia), 1% w/v Beef extract (Himedia) and 0.5% NaCl). Production was carried out by inoculating with an inoculum size of 1% v/v from a 24 hrs old culture broth (Concentration 1 mg/ml) in 50 ml of Nutrient broth and kept for incubation at 30° C.-40° C. for 24 hrs at 160-200 rpm. Activity was determined by ninhydrin assay.

Determination of BSH

1. Qualitative method Plate assay: Agar plates with required growth medium for the organism were prepared. 0.7% of Bile salt Mixture (Himedia) was added to the test plate. After 72 hrs of incubation at 30° C.-40° C., test and control plate were compared. White precipitation was observed in the test plate indicating positive strain for BSH production.

2. Quantitative method Ninhydrin assay: 2 ml of test culture was taken and centrifuged at 10,000 rpm for 5 min. The pellet was washed with 0.1M Sodium phosphate buffer, pH6. After centrifugation at 10,000 rpm for 5 min pellet was re-suspended in reaction mixture comprising of 180 µl of 0.1M Sodium phosphate buffer, pH6 and 20 µl of 10 mM glycochenodeoxy cholic acid (Sigma chem). Reaction mixture was kept for incubation at 40° C. for 1 hr. Reaction was quenched by addition of 200 µl (15% v/v) Trichloroacetic acid (TCA) and centrifuged at 10000 rpm for 5 min. 20 µl of supernatant was mixed with 20 µl of ninhydrin reagent (Sigma chem) and was kept for incubation in boiling water bath at 100° C. for 10 mins. O.D was measured at 570 nm by addition of 1.960 ml of double distilled water to the mixture. Activity was calculated.

Example 3a

Organisms Screened Positive for BSH Activity

Using plate assay method 16 lactobacillus strains (L. plantarum ATCC.NO-8014, L. fermentum ATCC.NO-9338, L. acidophillus ATCC.NO-11975, L. buchneri ATCC.NO-4005, L. brevis ATCC.NO-13648, L. casei ATCC.NO-335, L. casei var rhamnous NCIM.NO-2125, L. delbrukii var delbrukii ATCC.NO-9649, L. jugurti NCIB.NO-2366, L. pentos NCIM.NO-2669, L. viridenscens ATCC.NO-12706, L. bulgarius ATCC.NO-8001, L. helviticus ATCC.NO-8018; L. lactis ATCC.NO-10705, L. lechimanni ATCC.NO-4797, L. species NCIM-2658), 5 Marine organisms and 4 penicillin acylase producing strains were screened for BSH activity in the manner as aforesaid.

Example 3b: Organisms Screened Positive by Ninhydrin Assay

The above organisms were further screened quantitatively using ninhydrin assay.

13 organism were selected by ninhydrin assay: Amongst the 5 isolated Marine strains, 7 strains of *Lactobacillus* (*L. plantarum* ATCC.NO-8014, *L. fermentum* ATCC.NO-9338, *L. acidophillus* ATCC.NO-11975, *L. casei* ATCC.NO-335, *L. bulgarius* ATCC.NO-8001, *L. lactis* ATCC.NO-10705, *L. lechimanni* ATCC.NO-4797) and 1 penicillin acylase producing strain (*Bacillus cereus* ATCC.No JN183063), the *Brevibacterium casei* AP9 strain (Accession No. MCC0012) showed highest activity of 2-2.5 IU. The organisms were further screened on the following basis.

Example 4: Acid Tolerance Test

13 Organisms (refer example 3b) were grown in respective medium (Medium for *Lactobacillus* organism was MRS (Himedia) broth and for marine strains and *Bacillus cereus* strain Nutrient broth medium was used) with varying pH (2 to 5). Growth and activity were monitored (0-96 hrs).

Results:

Marine organism i.e. *Brevibacterium casei* (AP9) showed survival and BSH activity of 1-1.5 IU, whereas no growth was observed for *Lactobacillus* strains in pH 3 and for penicillin acylase producing strain at pH 4 (Table 1).

TABLE 1

| Acid tolerance test | | | | | |
|---|---|---|---|---|---|
| | | 24 hrs | 48 hrs | 72 hrs | 96 hrs |
| *B. Casei* AP9 | | | | | |
| pH 2 | Activity | — | — | — | — |
| | O.D at 600 nm | — | — | — | — |
| pH 3 | Activity | — | Low biomass | 0.185 | 0.65 |
| | O.D at 600 nm | — | 0.245 | 0.561 | 0.79 |
| pH 4 | Activity | Low biomass | 0.11 | 0.56 | 0.86 |
| | O.D at 600 nm | 0.245 | 0.56 | 0.66 | 0.89 |
| pH 5 | Activity | 0.12 | 0.72 | 1.15 | 1.5 |
| | O.D at 600 nm | 0.56 | 0.89 | 1.1 | 1.21 |
| *L. acidophillus* | | | | | |
| pH 2 | Activity | — | — | — | — |
| | O.D at 600 nm | — | — | — | — |
| pH 3 | Activity | — | — | — | — |
| | O.D at 600 nm | — | — | — | — |
| pH 4 | Activity | — | Low biomass | Low biomass | 0.13 |
| | O.D at 600 nm | — | 0.145 | 0.361 | 0.589 |
| pH 5 | Activity | Low biomass | Low biomass | 0.345 | 0.89 |
| | O.D at 600 nm | 0.145 | 0.461 | 0.745 | 0.9361 |
| *L. bulgarius* | | | | | |
| pH 2 | Activity | — | — | — | — |
| | O.D at 600 nm | — | — | — | — |
| pH 3 | Activity | — | — | — | — |
| | O.D at 600 nm | — | — | — | — |
| pH 4 | Activity | — | — | Low biomass | Low biomass |
| | O.D at 600 nm | — | — | 0.18 | 0.34 |
| pH 5 | Activity | — | Low biomass | 0.14 | 0.34 |
| | O.D at 600 nm | — | 0.18 | 0.51 | 0.78 |
| *B. cereus* | | | | | |
| pH 2 | Activity | — | — | — | — |
| | O.D at 600 nm | — | — | — | — |
| pH 3 | Activity | — | — | — | — |
| | O.D at 600 nm | — | — | — | — |
| pH 4 | Activity | — | — | — | — |
| | O.D at 600 nm | — | — | — | — |
| pH 5 | Activity | Low biomass | Low biomass | 0.42 | 0.75 |
| | O.D at 600 nm | 0.18 | 0.34 | 0.68 | 0.84 |

Example 5: Bile Salt Tolerance Test

13 Organisms (refer example 3b) with reference to example 4 were grown in respective (Medium for *Lactobacillus* organism was MRS (Himedia) broth and for marine strains and *Bacillus cereus* strain Nutrient broth medium was used) medium with varying Bile Salt concentration (0.5-5.5%). Growth and activity were monitored (0-72 hrs).

Results:

*Lactobacillus* strains (refer example 3b) showed tolerance of 2% with activity of 0.1-0.5 IU, penicillin acylase producing strain exhibited (refer example 3b) 5% tolerance with activity of 0.1-2 IU, 2 strains showed 3% and 7% tolerance with activity of 0.1-2.5 IU and 0.1-2 IU respectively and *Brevibacterium casei* AP (Accession No: MCC0012) showed a tolerance of 1% with activity 0.75-1.25 IU. These results were considered in favor of *Brevibacterium casei* AP (Accession No: MCC0012) as human gut has 0.3% concentration of bile salts.

Example 6a: Sodium Chloride Salt Tolerance Test

13 Organisms (refer example 3b) were grown in respective medium (Medium for *Lactobacillus* organism was MRS (Himedia) broth and for marine strains and *Bacillus cereus* strain Nutrient broth medium was used) with different salt concentration (2-22%) to check their viability and activity at high salt concentrations.

Results:

*Brevibacterium casei* AP9 (Accession No MCC0012) demonstrated maximum tolerance of 18-22% with activity of 1.75-2.5 IU. *Lactobacillus* strain (refer example 3b) showed a tolerance of 6-8% with activity of 1.5-2 IU and penicillin acylase producing strain (refer example 3b) exhibited 8-10% tolerance with activity of 1.75-2.5 IU.

Example 6b

Based on the above results, 4 organisms were considered for carrying out further studies viz., 2 strains of *Lactobacillus* (*L. acidophillus* ATCC NO 11975 and *L. bulgarius* ATCC NO 8001) as control strains, 1 Marine organism (*Brevibacterium casei* AP9 (Accession No MCC0012) and 1 strain of penicillin acylase producing (*Bacillus cereus* ATCC No JN183063).

Example 7: Evaluation of Other Probiotic Properties

For an organism to be used as a probiotic, it should satisfy some of the important probiotic properties. The following tests were carried out on all 4 strains (refer Example 6b):

1. Resistance to Gastric and Intestinal Fluid:

50 ml of respective medium (Medium for *Lactobacillus* organism was MRS (Himedia) broth and for *Brevibacterium casei* AP9 (Accession No MCC0012 and *Bacillus cereus* strain Nutrient broth medium was used) were inoculated at 1% (v/v) culture of aforementioned strains and incubated for 24 h. After washing in sterile saline solution (NaCl, 0.9%) and centrifugation at 10,000 rpm for 5 min, the cell suspensions were added to 50 ml of artificial gastric juice with the following composition: NaCl, 125 mmol/l; KCl, 7 mmol/l; $NaHCO_3$, 45 mmol/l and pepsin, 3 g/l (Sigma). The final pH was adjusted with HCl to pH 2 and 3 and with NaOH to pH 7. The bacterial suspensions were incubated with agitation (200 rev min/l) to simulate peristalsis. Aliquots were taken for the enumeration of viable counts at 0, 90 and 180 min. The effect of gastric digestion was also determined by suspending the cells in skimmed milk instead of saline solution before the inoculation of gastric juice at pH 2. Simulated intestinal fluid was prepared by suspending the cells (after 180 min of gastric digestion) in 0.1% (wt/v) Pancreatin (Sigma) and 0.15% (w/v) Bile salts mixture (Sigma) in water and adjusting it to pH 8.0 with 5 mol/l NaOH. The suspensions were incubated as above and samples for total viable counts were taken at 0, 90 and 180 min. (Table 2).

TABLE 2

| | Wash with NaCl | | | |
|---|---|---|---|---|
| | Time (min) | pH 7 Number of Initial cell (CFU/mL) | pH 3 Number of Initial cell (CFU/mL) | pH 2 Number of Initial cell (CFU/mL) |
| *Brevibacterium casei* AP9 (Accession No MCC0012) | | | | |
| Gastric Fluid | 0 | 6.2 | 5.92 | 5.98 |
| | 90 | 6.2 | 5.86 | 5.85 |
| | 180 | 6.16 | 5.8 | 5.8 |
| Intestinal fluid pH 8 | 0 | 6.14 | 5.9 | 5.9 |
| | 90 | 6.13 | 5.86 | 5.86 |
| | 180 | 6.12 | 5.84 | 5.84 |
| *B. cereus* (re: Example 6b) | | | | |
| Gastric Fluid | 0 | 6.2 | 6.2 | 6 |
| | 90 | 6.2 | 6.2 | 6 |
| | 180 | 6.2 | 6.2 | 6 |
| Intestinal fluid pH 8 | 0 | 6.2 | 3.1 | 2.85 |
| | 90 | 6.2 | 3.05 | 2.6 |
| | 180 | 6.2 | 3 | 2.53 |
| *L. acidophillus* (re: Example 6b) | | | | |
| Gastric Fluid | 0 | 6.2 | 6.2 | 6 |
| | 90 | 6.2 | 6.2 | 4.5 |
| | 180 | 6.2 | 6.2 | 3 |
| Intestinal fluid pH 8 | 0 | 6.2 | 6 | 2.25 |
| | 90 | 6.2 | 5.8 | 1.75 |
| | 180 | 6.2 | 5.5 | 1.2 |
| *L. bulgarius* (re: Example 6b) | | | | |
| Gastric Fluid | 0 | 6.2 | 6.2 | 6 |
| | 90 | 6.2 | 6.2 | nil |
| | 180 | 6.2 | 6.2 | nil |
| Intestinal fluid pH 8 | 0 | 6.2 | 5.5 | nil |
| | 90 | 6.2 | 5.3 | nil |
| | 180 | 6.2 | 5.1 | nil |

TABLE 3

| | Skimmed milk wash | | | |
|---|---|---|---|---|
| | Time (min) | pH 7 Number of Initial cell (CFU/mL) | pH 3 Number of Initial cell (CFU/mL) | pH 2 Number of Initial cell (CFU/mL) |
| *Brevibacterium casei* AP9 (Accession No MCC0012) | | | | |
| Gastric Fluid | 0 | 6.2 | 5.92 | 5.98 |
| | 90 | 6.2 | 5.9 | 5.9 |
| | 180 | 6.16 | 5.9 | 5.85 |
| Intestinal fluid pH 8 | 0 | 6.15 | 5.9 | 5.8 |
| | 90 | 6.15 | 5.87 | 5.792 |
| | 180 | 6.15 | 5.85 | 5.8 |
| *L. acidophillus* (re: Example 6b) | | | | |
| Gastric Fluid | 0 | 6.2 | 6.2 | 6 |
| | 90 | 6.2 | 6.2 | 6 |
| | 180 | 6.2 | 6.2 | 6 |
| Intestinal fluid pH 8 | 0 | 6.2 | 5.9 | 6 |
| | 90 | 6.2 | 5.7 | 2.9 |
| | 180 | 6.2 | 5.65 | 1.4 |
| *B. cereus* (re: Example 6b) | | | | |
| Gastric Fluid | 0 | 6.2 | 6.2 | 6 |
| | 90 | 6.2 | 6.2 | 6 |
| | 180 | 6.2 | 6.2 | 6 |
| Intestinal fluid pH 8 | 0 | 6.2 | 6.2 | 5.8 |
| | 90 | 6.2 | 6.2 | 5.2 |
| | 180 | 6.2 | 6.2 | 5.5 |
| *L. bulgarius* (re: Example 6b) | | | | |
| Gastric Fluid | 0 | 6.2 | 6.2 | 6 |
| | 90 | 6.2 | 6.2 | 6 |
| | 180 | 6.2 | 6.2 | 2.3 |
| Intestinal fluid pH 8 | 0 | 6.2 | 6 | 1.2 |
| | 90 | 6.2 | 5.9 | 0.6 |
| | 180 | 6.2 | 5.7 | nil |

Conclusion

Table 2 indicates that *Brevibacterium casei* AP-9 (Accession No: MCC0012) has better survival in gastric intestinal fluid as compared to other strains. These data illustrate that the organism *Brevibacterium casei* AP-9 (Accession. No: MCC0012) survives through the harsh condition of the digestive system to reach the intestinal track for further adhesion. The study also proves that *Brevibacterium casei*

AP-9 (Accession No: MCC0012 has a better survival rate as compared to frequently used probiotic strain *L. acidophillus* (re: Example 6b).

2. Adhesion Properties

A. Plain Adhesion

To reduce the harsh effects of GI fluid, the culture was washed with skimmed milk. Table 3 shows the enhanced effect of the skimmed milk where the CFU/ml has decreased considerably low as compared to that of the NaCl wash, especially in the pH 2 range. Thus skimmed milk also enhances the survival of *Brevibacterium casei* AP-9 (Accession No: MCC0012).

Mucin plate preparations: 100 µL of a 10 mg/mL solution of partially purified type III porcine gastric mucin (Sigma-Aldrich) was immobilized in 96-well microtiter plates by incubation overnight at 4° C. Excess mucin was removed by pipetting, and the wells were washed twice with 200 µL of phosphate buffer solution. Preparations of freshly grown cultures (24 hr incubation) were used for the adhesion assay. 100 µL of culture were added to each well. The plates were then incubated for 3 h at 37° C. Each well was washed five times with 200 µL of sterile phosphate buffered saline (PBS) to remove unbound bacteria and then treated with 200 µL of a 0.05% (v/v) Triton X-100 (Sigma-Aldrich) solution to desorb the bound bacteria. Aliquots were taken from the solution for enumeration and the results are shown in table 4.

TABLE 4

Results of percentage Adherence of bacteria

| | Number of Initial cell (CFU/mL) | Number of final cell (CFU/mL) | % Adhered |
|---|---|---|---|
| *L. acidophillus* (re: Example 6b) | 11.44 ± 0.03 | 8.59 ± 0.24 | 75.35 |
| *L. plantarum* (re: Example 6b) | 11.7 ± 0.10 | 8.56 ± 0.084 | 73.16 |
| *B. cereus* (re: Example 6b) | 12.466 ± 0.05 | 9.33 ± 0.085 | 74.87 |
| *Brevibacterium casei* AP-9 (Accession No: MCC0012) | 10.7 ± 0.4 | 8.55 ± 0.317 | 79.9 |

*Experiments carried out in triplicates. Cell count expressed in the form Mean ± Standard error of mean Conclusion:

The above data indicates that *Brevibacterium casei* AP-9 (Accession No: MCC0012) has a better adhesion rate as compared to frequently used probiotic strain *L. acidophillus* (refer Example 6b).

B. Adhesion in Presence of Gastric and Intestinal Fluids

The experiment was carried out on the same basis as the plain adhesion experiment. Modification was done in the 100 µL sample, as follows: Preparations of freshly grown cultures (24 hr incubation) were used for adhesion assay. One ml of culture was mixed with 1 ml of gastric and intestinal fluid separately, from this mixture 100 µl was added to each well. The experiment was further carried out as plain adhesion and the results were depicted in table 5.

TABLE 5

Results of percentage adherence of bacteria in the presence of gastric and intial fluids

| | pH7 | | | pH3 | | | pH2 | | | Intestinal fluid | | |
|---|---|---|---|---|---|---|---|---|---|---|---|---|
| | Number of intial cell (CFU/mL) | Number of final cell (CFU/mL) | % Adhered | Number of intial cell (CFU/mL) | Number of final cell (CFU/mL) | % Adhered | Number of intial cell (CFU/mL) | Number of final cell (CFU/mL) | % Adhered | Number of intial cell (CFU/mL) | Number of final cell (CFU/mL) | % Adhered |
| *L. acidophillus* | 8.949 ± 0.02 | 7.79 ± 0.17 | 87.04 | 8.949 ± 0.02 | 8.39 ± 0.24 | 93.75 | 8.949 ± 0.02 | 8.59 ± 0.24 | 96.21 | 8.949 ± 0.02 | 8.32 ± 0.1 | 92.97 |
| *L. plantarum* | 8.86 ± 0.126 | 8.56 ± 0.084 | 95 | 8.86 ± 0.126 | 8.385 ± 0.042 | 94.86 | 8.86 ± 0.126 | 8.56 ± 0.084 | 87 | 8.86 ± 0.126 | 0 ± 0 | 0 |
| *B. cereus* | 8.81 ± 0.067 | 9.33 ± 0.085 | 88.53 | 8.81 ± 0.067 | 8.316 ± 0.14 | 94.39 | 8.81 ± 0.067 | 9.33 ± 0.085 | 91.94 | 8.81 ± 0.067 | 8.6 ± 0.05 | 97.61 |
| AP7 | 14.76 ± 0.46 | 14.236 ± 0.09 | 96.43 | 14.82 ± 0.05 | 14.62 ± 0.17 | 98.65 | 14.76 ± 0.03 | 14.24 ± 0.189 | 96.47 | 15.05 ± 0.02 | 14.47 ± 0.309 | 96.14 |
| AP9 | 14.63 ± 0.164 | 13.98 ± 0.2 | 95.5. | 14.59 ± 0.56 | 13.89 ± 0.23 | 95.2 | 14.43 ± 0.1 | 14.1 ± 0.259 | 98.6 | 15.18 ± 0.38 | 14.07 ± 0.031 | 92.68 |

*Experiments carried out in triplicates. Cell count expressed in the form Mean ± Standard error of mean Conclusion:

The above data indicates that *Brevibacterium Casei* AP-9 (Accession No: MCC0012) has an equivalent adhesion rate to mucin layer in presences Gastric and intestinal fluids compared to frequently used probiotic strain *L. acidophillus* (refer Example 6b)

3. Antibacterial Activity

Antibacterial activity of the cultures [refer example 6b] was evaluated by the disc-diffusion assay. Test cultures of *Escherichia coli* ATCC.NO 8739, *Staphylococcus aureus* NCIB NO 2079 and NCTC NO 7447, *Klebsiella pneumonia* NCTC NO 418, *Klebsiella aeroginesa* ATCC NO 2098, *Bacillus subtilis* ATCC 6633, *Salmonella abony* NCTC NO 6017, were obtained from National Collection of Industrial Microorganisms (NCIM).

Disc Diffusion Method:

1. Plain antimicrobial: 20 µL of culture broth of cultures referred to in example 6b was applied to sterile filter discs (6-mm) which were placed on the surface of 100 µL of test microorganisms that had been cultured for 12-14 h on nutrient agar. The plates were incubated at 30° C.-40° C. for 14-16 h and the diameter of zones of inhibition then measured.

Results:

The radius of the zone of inhibition for *Brevibacterium casei* AP-9 (Accession No: MCC0012) ranged from 1.8-0.8 cm, *L. acidophilus* 1.6-0.6 cm, *L. bulgarius* 1.35-1.05 cm, *B. cereus* 1.7-1.2 cm.

Conclusion:

The above zone of inhibition data indicates that *Brevibacterium casei* AP-9 (Accession No: MCC0012) has an edge in antibacterial activity when compared to frequently used probiotic strain *L. acidophillus*.

Antimicrobial Activity in Presence of 0.5% and 0.15% Bile Salts:

20 μL of culture broth of cultures referred to in example 6b was applied to sterile filter discs (6 mm) which were placed on the surface of 100 μL of test microorganisms that had been cultured for 12-14 hrs on nutrient agar containing 0.15% and 0.5% Bile salts. The plates were incubated at 30° C.-40° C. for 14-16 h and the diameter of zones of inhibition then measured.

Results:

The radius of the zone of inhibition for *Brevibacterium casei* AP-9 (Accession No: MCC0012) ranged from 1.3-0.9 cm, *L. acidophilus* 1-0.8 cm, *L. bulgarius* 1.2-0.5 cm, *B. cereus* 1-1.3 cm.

Conclusion:

The above Zone of inhibition data is in presence of bile salt concentration indicates that *Brevibacterium casei* AP-9 (Accession No: MCC0012) still has an edge in antibacterial activity when compared to frequently used probiotic strain *L. acidophillus*. This also indicates that *Brevibacterium casei* AP-9 (Accession No: MCC0012) does not lose its antibacterial activity in presences of bile salts.

Antimicrobial Activity in Presence of 6% NaCl:

20 μL of culture broth of cultures referred to in example 6b was applied to sterile filter discs (6 mm) which were placed on the surface of 100 μL of test microorganisms that had been cultured for 12-14 h on nutrient agar containing 6% NaCl salts. The plates were incubated at 30° C.-40° C. for 14-16 h and the diameter of zones of inhibition then measured.

Results:

The radius of the zone of inhibition for *Brevibacterium casei* AP-9 (Accession No: MCC0012) ranged from 2.85-1 cm, *L. acidophilus* 1.8-1 cm, *L. bulgarius* 2.3-0.8 cm, *B. cereus* 3.3-1.2 cm.

TABLE 6

| | B. subtillus | E. coli | K. pneumoniae | K. aeroginesa | S. abony | S. aureus |
|---|---|---|---|---|---|---|
| L. acidophillus | 1.23 ± 0.44 | 1.167 ± 0.21 | 1.58 ± 0.29 | 0.6 ± 0.1 | 1.58 ± 0.21 | 0.958 ± 0.16 |
| L. bulgarius | 1.13 ± 0.06 | 1.33 ± 0.09 | 1.28 ± 0.14 | 1.12 ± 0.06 | 1.26 ± 0.08 | 1.26 ± 0.03 |
| B. casei AP9 | 0.82 ± 0.07 | 1.56 ± 0.22 | 1.76 ± 0.10 | 1.26 ± 0.10 | 1.42 ± 0.19 | 1.25 ± 0.024 |
| B. cereus | 1.26 ± 0.03 | 1.32 ± 0.33 | 1.68 ± 0.16 | 1.57 ± 0.18 | 1.50 ± 0.08 | 1.35 ± 0.21 |

The diameter of inhibition zone given in mm excluded the size of the filter disc (6 mm).
(mean ± standard deviation, n = 3)

TABLE 7

| | B. subtillus | E. coli | K. pneumoniae | K. aeroginesa | S. abony | S. aureus |
|---|---|---|---|---|---|---|
| L. acidophillus | 1 ± 0.2 | 0.83 ± 0.04 | 0.2 ± 0.08 | 0.72 ± 0.2 | 1.06 ± 0.05 | 1 ± 0.05 |
| L. bulgarius | 1 ± 0.09 | 0.92 ± 0.04 | 0.67 ± 0.4 | 1.02 ± 0.06 | 1.13 ± 0.06 | 1.14 ± 0.08 |
| B. cereus | 1.2 ± 0.31 | 1.28 ± 0.21 | 1 ± 0.21 | 1.12 ± 0.14 | 1 ± 0.1 | 1.05 ± 0.02 |
| B. casei AP9 | 0.95 ± 0.06 | 1.15 ± 0.1 | 0.93 ± 0.04 | 1.26 ± 0.19 | 1.28 ±0.03 | 0.98 ± 0.03 |

The diameter of inhibition zone in presences of bile salts given in mm excluded the size of the filter disc (6 mm).
(mean ± standard deviation, n = 3)

TABLE 8

| | B. subtillus | E. coli | K. pneumoniae | K. aeroginesa | S. aureus |
|---|---|---|---|---|---|
| L. acidophillus | 1 ± 0.02 | 1.62 ± 0.08 | 1.8 ± 0.27 | 1.16 ± 0.15 | 1.1 ± 0.05 |
| L. bulgarius | 1.06 ± 0.02 | 2.35 ± 0.14 | 0.8 ± 0.42 | 1.29 ± 0.6 | 1.12 ± 0.07 |
| B. casei AP9 | 0.98 ± 0.04 | 1.65 ± 0.3 | 1.4 ± 0.07 | 0.95 ± 0.13 | 1.39 ± 0.06 |
| B. cereus | 1.215 ± 0.02 | 3.3 ± 0.28 | 1.4 ± 0.13 | 2.6 ± 0.023 | 1.34 ± 0.01 |

The diameter of inhibition zone in presences of NaCl salts given in mm excluded the size of the filter disc (6 mm).
(mean ± standard deviation, n = 3)

Conclusion:

The above zone of inhibition data is in the presence of Sodium salt concentration and indicates that *Brevibacterium casei* AP-9 (Accession No: MCC0012) still has an edge in antibacterial activity when compared to frequently used probiotic strain *L. acidophilus*. This also indicates that *Brevibacterium casei* AP-9 (Accession No: MCC0012) does not lose its antibacterial activity in the presence of sodium salts.

Example 8

Cholesterol Reduction:

Reduction of cholesterol was carried out by growing *Brevibacterium casei* in the presence of extracellular cholesterol and deconjugation of bile salts i.e. by interference in the enterohepatic pathway. Bile is composed mainly of bile salts, it is produced by liver cells and secreted into the duodenum via the bile duct. Cholesterol is the precursor of primary bile salts that are formed in the liver and stored as conjugated bile salts in the gall bladder for secretion in the gastrointestinal tract. Deconjugated bile salts are more hydrophobic than conjugated bile salts, resulting in lower absorption in the intestinal lumen and are lost in feces. Thus in a steady state situation, deconjugation of bile salts can reduce serum cholesterol levels by increasing the formation of new bile salts that are needed to replace those that have escaped the enterohepatic circulation.

Evaluation of Reduction in Extracellular Cholesterol:

Freshly prepared nutrient broth was supplemented with 0.30% oxgall as a bile salt. Water soluble cholesterol (polyoxyethanyl-cholesteryl sebacate) was filter sterilized and added to the Nutrient broth at a final concentration of 100 µg/ml. The medium was inoculated with *Brevibacterium casei* AP9 at 1% level and incubated at 350° C. for 20 h. After the incubation period, cells were centrifuged and the remaining cholesterol concentration in the broth was determined using a modified colorimetric method. One milliliter of the aliquot was added with 1 mL of KOH (33% wt/vol) and 2 mL of absolute ethanol, vortexed for 1 min, followed by heating at 370° C. for 15 min. After cooling, 2 mL of distilled water and 3 mL of hexane were added and vortexed for 1 min. One milliliter of the hexane layer was transferred into a glass tube and evaporated under nitrogen. The residue was immediately dissolved in 2 mL of o-phthalaldehyde reagent. After complete mixing, 0.5 mL concentrated sulphuric acid was added and the mixture was vortexed for 1 min. Absorbance was read at 550 nm after 10 min. The absorbance obtained was compared with a standard graph of cholesterol. All experiments were replicated twice and the results obtained were interpreted from the standard graph for cholesterol detection as depicted in FIG. 1.

The reduction in cholesterol was detected by using initial and final concentration of cholesterol in the broth.

Initial concentration of cholesterol=95 µg/ml (Blank)
Final concentration of cholesterol=35 µg/ml Hence 60% of extracellular cholesterol was reduced by *Brevibacterium casei* AP9.

Evaluation of Deconjugation of Bile Acids:

10 ml volumes of Nutrient broth were supplemented with 6 mM sodium glycocholate, 6 mM sodium taurocholate or a combination of sodium glycocholate and sodium taurocholate at 2.8 mM and 1.2 mM, respectively. Individual bile salts were added as 6 mM each, because it resembles the concentrations prevailing in the human small intestine while bile mixtures containing 2.8 mM sodium, glycocholate and 1.2 mM sodium taurocholate resemble the molar ratio of the two salts in human bile. *Brevibacterium casei* AP9 was inoculated at 1% level and incubated at 350° C. for 20 hrs. Bile salt deconjugation ability was based on release of deconjugated bile. The following method was used to measure the amount of free cholic acid released by each organism. Briefly, 10 mL of the culture of the organism after the incubation period was adjusted to pH 7.0 with NaOH (1 N). Cells were centrifuged at 8000 rpm at 4° C. for 10 min. Supernatant obtained was adjusted to pH 1.0 with HCl (10 N). One milliliter of the supernatant was added with 2 mL of ethyl acetate and the mixture was vortexed for 1 min. Two milliliters of the ethyl acetate layer were transferred into a glass tube and evaporated under nitrogen at 600° C. The residue was immediately dissolved in 1 mL of NaOH (0.01 N). After complete mixing, 1 mL of furfuraldehyde (1%) and 1 mL, of $H_2SO_4$ (16 N) were added, and the mixture was vortexed for 1 min before heating at 650° C. in a water bath for 10 min. After cooling, 2 mL of glacial acetic acid was added and the mixture was vortexed for 1 min. Absorbance was read at 660 nm. The amount of cholic acid released was determined using cholic acid as a standard (Sigma Chemical). All experiments were replicated twice and the results obtained were interpreted from a standard graph for cholic acid detection as illustrated in FIG. 2.

Reduction in Bile salts observed are as follows:
1. Sodium glycocholate hydrate
   Initial concentration=6 mM
   Final concentration=0.87 mM
2. Sodium taurocholate hydrate
   Initial concentration=6 mM
   Final concentration=0.32 mM
3. Mixture of Bile salts
   Initial concentration=4 mM
   Final concentration=0.9 mM The above data indicates 85% deconjugation of Sodium glycocholate hydrate, 94.6% deconjugation of Sodium taurocholate hydrate and 78% deconjugation of mixture of bile salts by *Brevibacterium casei* AP9.

These in-vitro results of reduction in extracellular cholesterol and deconjugation of bile salts support the fact that *Brevibacterium casei* AP9 of the instant invention is capable of reducing food cholesterol and also serum cholesterol by interference in enterohepatic pathway. The higher percentage of deconjugation is observed due to higher production of Bile salt hydrolase enzyme by the bacteria. The above data would serve the purpose of *Brevibacterium casei* AP9's use in a probiotic formulation that would lower cholesterol substantially.

Advantages of the Invention

Novel organisms isolated
Organism is resistant to acid, bile, gastric and intestinal juices
Organism possess anti-microbial properties
Organism is capable of reducing cholesterol

The invention claimed is:

1. A probiotic composition comprising an isolated bacterial strain of *Brevibacterium casei* AP9, deposited at NCCS, Pune, India under the Budapest Treaty, and having accession number MCC0012, and a hydrocolloid, and optionally, one or more additional probiotic organisms that enhance the probiotic activity of the *Brevibacterium casei* MCC0012.

2. The probiotic composition as claimed in claim 1, wherein the composition comprises the one or more additional probiotics and the one or more additional probiotics are selected from the group consisting of *L. plantarum* ATCC number 8014, *L. fermentum* ATCC number 9338, *L acidophillus* ATCC number 11975, *L. casei* ATCC number 335, *L. bulgarius* ATCC number 8001, *L. lactis* ATCC number 10705, *L. lechimanni* ATCC number 4797 and *Bacillus cereus* ATCC number JN183063.

3. The probiotic composition as claimed in claim 1, wherein the hydrocolloid is selected from the group consisting of alginate, whey protein, gelatin, and carrageenan.

4. The probiotic composition as claimed in claim 1, wherein the composition is in solid, liquid or semisolid form.

5. The probiotic composition as claimed in claim 1, wherein the composition comprises $10^5$ to $10^9$ CFU/ml of *Brevibacterium casei* AP9 MCC0012.

6. The probiotic composition as claimed in claim 1, wherein the composition comprises 0.01 to 99.9% *Brevibacterium casei* MCC0012.

7. A method of providing probiotic therapy for reducing extracellular cholesterol, which comprises administering to a subject in need thereof a therapeutically effective amount of a composition that comprises *Brevibacterium casei* AP9 MCC0012.

8. The method of claim 7, wherein the composition further comprises a hydrocolloid.

9. The method of claim 7, wherein the composition further comprises one or more additional probiotic organisms that enhance the probiotic activity of the *Brevibacterium casei* AP9 MCC0012.

10. The method of claim 7, wherein the composition further comprises both a hydrocolloid and one or more additional probiotic organisms that enhance the probiotic activity of the *Brevibacterium casei* AP9 MCC0012.

* * * * *